US008070928B2

(12) United States Patent
Sundberg et al.

(10) Patent No.: US 8,070,928 B2
(45) Date of Patent: Dec. 6, 2011

(54) NANOFABRICATED STRUCTURES FOR ELECTRIC FIELD-ASSISTED NUCLEIC ACID EXTRACTION

(75) Inventors: Steven A. Sundberg, San Francisco, CA (US); Xing Su, Cupertino, CA (US); Grace Credo, San Mateo, CA (US)

(73) Assignee: Intel Corporation, Santa Clara, CA (US)

( * ) Notice: Subject to any disclaimer, the term of this patent is extended or adjusted under 35 U.S.C. 154(b) by 668 days.

(21) Appl. No.: 11/967,657

(22) Filed: Dec. 31, 2007

(65) Prior Publication Data
US 2009/0166205 A1    Jul. 2, 2009

(51) Int. Cl.
G01N 27/26    (2006.01)
B01D 27/02    (2006.01)

(52) U.S. Cl. ........ 204/600; 204/554; 204/450; 422/502; 435/6.1

(58) Field of Classification Search .......... 204/400–435, 204/600–668; 422/50–99, 502; 435/6; 436/6.1
See application file for complete search history.

(56) References Cited

U.S. PATENT DOCUMENTS

| | | | | |
|---|---|---|---|---|
| 7,135,144 | B2 * | 11/2006 | Christel et al. | 422/99 |
| 2003/0026740 | A1 * | 2/2003 | Staats | 422/102 |
| 2005/0242017 | A1 * | 11/2005 | Staats | 210/198.2 |
| 2006/0205093 | A1 * | 9/2006 | Prins | 436/526 |

OTHER PUBLICATIONS

Christel, L. A., Petersen, K. McMillan, W., Northrup, M. A., "Rapid, Automated Nucleic Acid Probe Assays Using Silicon Microstructures for Nucleic Acid Concentration," Journal of Biomechanical Engineering, 1999, 22-27, vol. 121.
Cady, N. C., Stelick, S., Batt, C. A., "Nucleic Acid Purification Using Microfabricated Silicon Structures," Biosensors and Bioelectronics, 2003, 59-66, vol. 19.
Volkmuth, W. D., Austin, R. H., "DNA Electrophoresis in Microlithographic Arrays," Nature, 1992, 600-602, vol. 358.
Yi, S., Seo, K.-S, Cho, Y.-H., "A DNA Trapping and Extraction Microchip Using Periodically Crossed Electrophoresis in a Micropillar Array," Sensors and Actuators A, 2005, 429-436, vol. 120.
Hu, Y., Li, D., "Modeling of Nucleic Acid Adsorption on 3D Prisms in Microchannels," Analytica Chimica Acta, 2007, 42-52, vol. 581.
Wang, Y.-C., Stevens, A. L., Han, J., "Million-fold Preconcentration of Proteins and Peptides by Nanofluidic Filter," Anal. Chem., 2005, 4293-4299, vol. 77(14).
Fu, J., Mao, P., Han, J., "Nanofilter Array Chip for Fast Gel-free Biomolecule Separation," Applied Physics Letters, 2005, 263902, vol. 87.
Fu, J., Schoch, R. B., Stevens, A. L., Tannenbaum, S. R., Han, J., "A Patterned Anisotropic Nanofluidic Sieving Structure for Continuous-flow Separation of DNA and Proteins," Nature Nanotechnology, 2007, 121-128, vol. 2.

* cited by examiner

*Primary Examiner* — Jeffrey T Barton
*Assistant Examiner* — Jennifer Dieterle
(74) *Attorney, Agent, or Firm* — Julia A. Hodge

(57) ABSTRACT

Embodiments of the invention provide devices and methods for extracting nucleic acid molecules from solution using electric fields. The structures and methods of embodiments of the invention are suited to incorporation into micro and nano fluidic devices, such as lab-on-a-chip devices and micro total analysis systems.

7 Claims, 4 Drawing Sheets

Side view of interdigitated structure
(concept drawing)

Side view of interdigitated structure
(concept drawing)

NANOFABRICATED STRUCTURES FOR ELECTRIC FIELD-ASSISTED NUCLEIC ACID EXTRACTION

BACKGROUND OF THE INVENTION

1. Field of the Invention

The embodiments of the present invention relate generally to structures and methods for extracting nucleic acids from multicomponent samples. The structures and methods of embodiments of the invention are suitable for incorporation into micro and nano fluidic devices, such as lab-on-a-chip devices and micro total analysis systems.

2. Background Information

Genetic information in living organisms is contained in the form of very long nucleic acid molecules such as deoxyribonucleic acid (DNA) and ribonucleic acid (RNA). Naturally occurring DNA and RNA molecules are typically composed of repeating chemical building blocks called nucleotides which are in turn made up of a sugar (deoxyribose or ribose, respectively), phosphoric acid, and one of four bases, adenine (A), cytosine (C), guanine (G), and thymine (T) or uracil (U). The human genome, for example, contains approximately three billion nucleotides of DNA sequence and an estimated 20,000 to 25,000 genes. DNA sequence information can be used to determine multiple characteristics of an individual as well as the presence of and or susceptibility to many common diseases, such as cancer, cystic fibrosis, and sickle cell anemia. Determination of the entire three billion nucleotide sequence of the human genome has provided a foundation for identifying the genetic basis of such diseases. Sequencing the genomes of individuals provides an opportunity to personalize medical treatments. The need for nucleic acid sequence information also exists in research, environmental protection, food safety, biodefense, and clinical applications, such as for example, pathogen detection (the detection of the presence or absence of pathogens or their genetic varients).

Accurate and precise separation of different molecules from one another is important in situations in which a small number of desired molecules are present as a mixture of several components in a small volume solution, such as, for example, in the context of analytical and diagnostic testing. Samples used in diagnostic tests, such as, for example bodily fluids and tissue samples, are typically mixtures of a variety of components. In order to perform accurate tests, the desired molecules must typically be separated from the components of the mixture. There remains a need to improve the efficiencies of such separations and, thereby, the convenience to researchers working in the chemical and biological sciences.

Because DNA sequencing is an important technology for applications in bioscience, such as, for example, the analysis of genetic information content for an organism, tools that allow for faster and or more reliable sequence determination are valuable. Applications such as, for example, population-based biodiversity projects, disease detection, personalized medicine, prediction of effectiveness of drugs, and genotyping using single-nucleotide polymorphisms, stimulate the need for simple and robust methods for sequencing nucleic. Methods and devices that provide increased accuracy and or robustness, decreased need for analysis sample, and or high throughput are valuable analytical and biomedical tools.

DETAILED DESCRIPTION OF THE INVENTION

Figure 1:
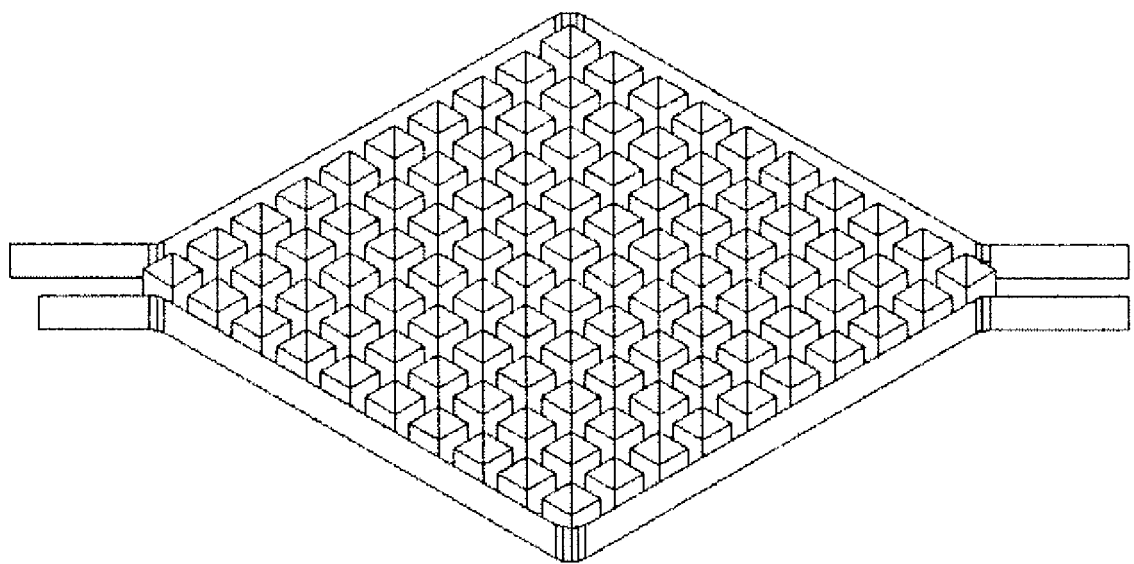
FIG. 1 provides an exemplary design for a nano fabricated structure useful for the extraction of nucleic acids from solution.

Embodiments of the present invention provide devices and methods for extracting, separating, removing, and or concentrating nucleic acid (or other) molecules from solutions and complex biological samples. Microfabricated and nanofabricated structures consisting of arrays of pillars form extraction columns for extraction of nucleic acid molecules (or other biological molecules) from crude biological samples, such as, for example, blood samples, cell lysates, urine, or saliva. Pillar arrays are incorporated into more complex, integrated microfluidic devices, for example, devices designed to extract nucleic acid from crude biological samples and perform sequencing-based or probe-based assays. The dimensions of the silicon pillars and the gaps between pillars for nanofabricated devices are in the range of tens to hundreds of nanometers.

Because the present invention uses scaleable microfabrication techniques and process-compatible materials to create structures of precise dimensions and controlled surface properties, it provides devices that are well suited to integration into microfluidic and nanofluidic devices. Fragments of nucleic acid found in crude biological preparations are typically large molecules (hundreds to thousands of base pairs in length) that have small diffusion coefficients (e.g. the diffusion coefficient for small to medium-sized DNA molecules ranges from $9.94 \times 10^{-7}$ cm$^2$/sec for single-stranded 18-mers to $1.97 \times 10^{-7}$ cm$^2$/sec for single-stranded 250-mers; the diffusion coefficients for large DNA molecules ranges from about $3.5 \times 10^{-9}$ cm$^2$/sec for double-stranded 2.1 kbp molecules to about $2.8 \times 10^{-9}$ cm$^2$/sec for double-stranded 164 kbp molecules). The use of microfabrication techniques to create structures with precise dimensions in the tens to hundreds of nanometers range enhances adsorption kinetics and improves both the efficiency and reproducibility of the extraction process.

Embodiments of the invention provide microfabricated and or nanofabricated structures consisting of pillar arrays with thin, conformal coatings of an insulating material such as, for example, silicon dioxide. An insulating coating provides the ability to apply electric fields across fluid-filled spaces to promote electrokinetic or electroosmotic transport of nucleic acid molecules (or other biological molecules) through an extraction space.

Alternate embodiments provide microfabricated and or nanofabricated structures consisting of pillar arrays having thin, conformal coatings of polymer or other process-compatible materials. Nucleic acids (or other biological molecules) that absorb to the polymer coatings on the surface of the pillars and are separated from solution. After the nucleic acids are separated from other solution components through absorption to the coating surface, they can then be eluted from the surface by, for example, switching to a different running buffer (i.e. one that differs in ionic strength, pH, etc.). Useful polymers include, for example, polymers that are able to alter their charge state in response to ambient conditions in which a change in pH causes the nucleic acid sample to deadsorb from the polymer surface. Polymers containing a selection of ionizable groups such as, for example, —COOH, —OH, —NH$_3$, —CH(NH$_3$)(COOH), —NRH$_2$, and —SH. Ionizable groups are chosen to create a polymer having a $pK_a$ that allows the target molecule to adsorb under a first set of conditions and deadsorb under a second set of conditions. The bio-molecule that is to be extracted from solution binds the polymer surface at one pH, in which the polymer is negatively charged, neutral, or positively charged, through electrostatic interaction, and then ambient conditions, such as pH or applied electric field, are changed causing the polymer to become differently charged and the bio-molecule to deadsorb from the surface due to reduced electrostatic attraction or electrostatic repulstion.

In embodiments of the invention microfabricated and or nanofabricated structures consisting of pillar arrays have thin, conformal coatings of an insulating material (e.g. silicon dioxide or other process-compatible material) typically bear ionizable functional groups. The $pK_a$ of the ionizable functional groups is shifted through the application of external electric fields in a manner that significantly changes the surface charge density of the pillar array thereby facilitating elution of nucleic acid molecules (or other biological molecules). External electric fields applied in the transverse direction to fluid flow are used to shift the $pK_a$ of functional groups on the surface of an insulating material coating the silicon pillars such that the surface charge density is significantly altered and adsorbed nucleic acid is released back into solution. Potential insulating materials include, for example, $SiO_2$ (silanol group $pK_a$=3.5), $ZrO_2$ (Zr—OH $pK_a$=6.7), $HfO_2$, hafnium silicates ($HfSi_xO_y$), zirconium silicates ($ZrSi_xO_y$), $Al_2O_3$, $La_2O_3$, and $Y_2O_3$.

Figure 2:
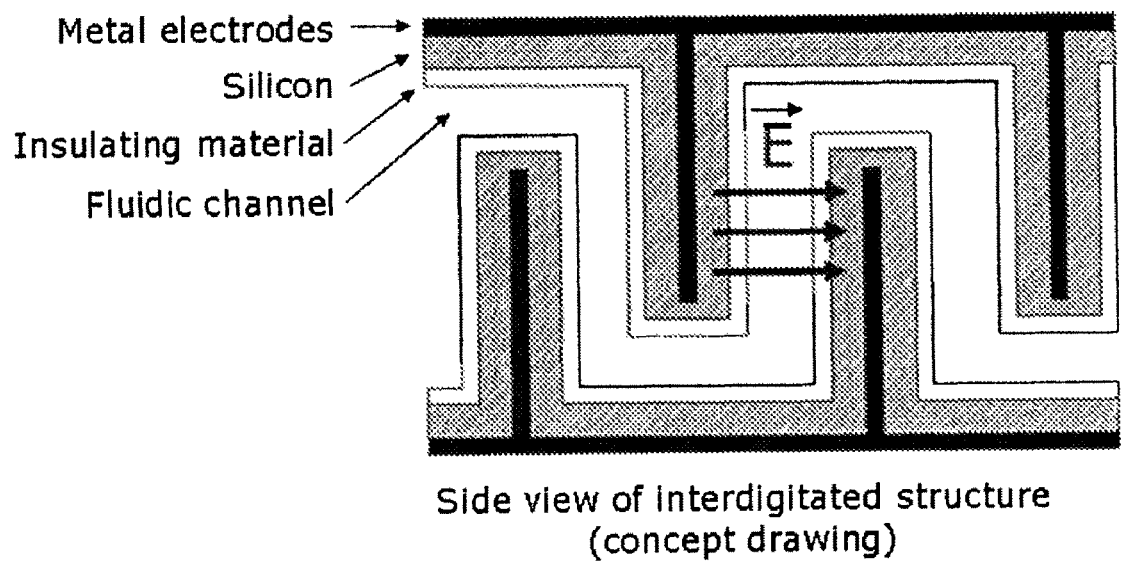
FIG. 2 provides a drawing of an exemplary device that can be used to extract nucleic acids from solution.

Nucleic acid extraction and elution is accomplished by flowing a sample through the device so that nucleic acid molecules adsorb to surfaces within the device and then are subsequently eluted from the device by means of a change in running buffer ionic strength or pH, or change in applied external electric fields. In additional embodiments, external electric fields applied along the axis of fluid flow are used for electrokinetic transport of nucleic acid molecules, thereby facilitating separation of the nucleic acid from other sample components and also overcoming the potentially large hydrodynamic flow resistance for a device having nanometer-scale fluid channel dimensions. Advantages of applied external electric fields include simplification of assay workflow and increased ease of functional integration in miniaturized assay device formats. External electric fields eliminate the need for a separate elution buffer because the nucleic acid or other charged molecule is eluted into the same running solution after adsorption by a change in the applied external electric field. Using thin, conformal coatings of an insulating material bearing ionizable functional groups, the nucleic acid or other charged molecule that has been adsorbed to the surface is eluted by applying an external electric field. The external electric field shifts the $pK_a$ of the functional groups, and hence the net charge on the surface of the coating, in such a way that adsorbed nucleic acid is directly eluted by means of electrostatic repulsion FIG. 1 shows an exemplary array of pillars, viewed from above. A fluid inlet and a fluid outlet are provided. The array of pillars is a structure that provides an increased surface area for extraction of nucleic acids or other charged molecules from solution through absorption to a surface and subsequent deabsorption. Other structures, such as that shown in FIG. 2 are possible. In FIG. 2 an electric field is applied across an interdigitated structure. Metal electrodes encased in silicon having a layer of an insulating material are capable of creating an electric field across the fluid channel.

FIG. 1 illustrates one design for a nanostructured device in which the dimensions of the silicon pillars and gaps between them are on the order of tens to hundreds of nanometers. Crude sample flows through the extraction column via the inlet and outlet. Nucleic acids adsorb to the silicon (or coated silicon) surfaces within the array. Adsorption kinetics are facilitated by means of the small dimensions (large surface area-to-volume ratio) of the device. In the simplest case, elution of extracted material takes place by means of changing the running buffer to one which neutralizes the molecular interactions between the nucleic acid fragments and the surface, for example, by changing the ionic strength of the buffer so that electrostatic repulsion is increased.

FIG. 2 provides a side view of a device in which an electric field can be applied across a channel. In this side view, silicon nanopillars are fabricated on two substrates that are bonded together to create an interdigitated structure of fluid channels. A thin insulating material, e.g., a layer of silicon dioxide or other suitable process-compatible material, is used to prevent current flow across the fluidic channel such that application of a electrical potential difference across the upper and lower metal electrodes creates an electrostatic potential at the insulator-solution interface. This electrostatic potential is used to shift the $pK_a$ of ionizable groups on the surface of the insulating material, e.g. silanol groups ($pK_a$=3.5) in the case of silicon dioxide. Optionally, the first of the two substrates additionally has a first channel (not shown) and a second channel (not shown) that allow a liquid to flow into and out of the third channel created by the interdigitation of the pillar arrays. Alternately and optionally, the first of the two substrates additionally has a first channel (not shown) and the second substrate has a second channel (not shown) that allow a liquid to flow into and out of the third channel created by the interdigitation of the first and second pillar arrays.

Figure 3:
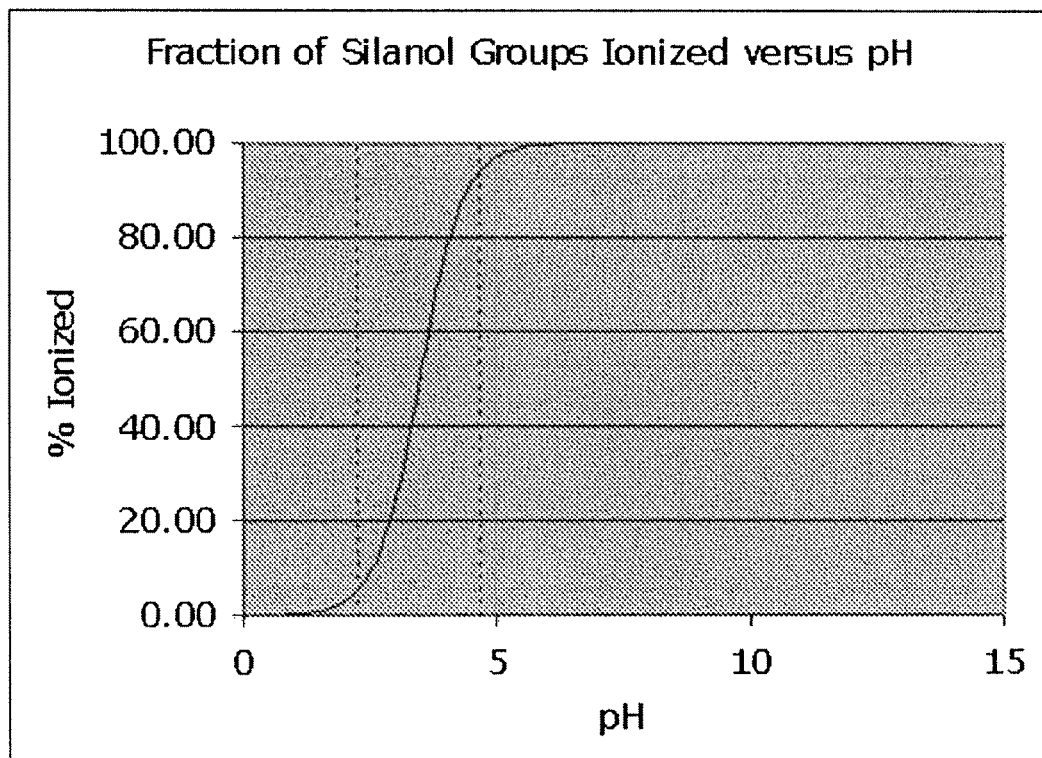
FIG. 3 graphs the percentage of silanol groups ionized as a function of the solution pH.

FIG. 3 graphs the percentage of silanol groups that are ionized (—SiOH↔—SiO$^-$+H$^+$) as a function of solution pH. The $pK_a$ of the silanol group is 3.5 for silicon dioxide silanol groups (—SiOH). For an insulating coating the magnitude of the $pK_a$ shift observed for surface —OH groups will be dependent on a number of parameters including the magnitude of the electrostatic potential at the insulator-solution interface, as well as solvation effects, and the pH and ionic strength of the buffer solution. From the Henderson-Hasselbach equation, the magnitude of pH change required to shift a surface bearing ionizable groups from 5% charged to 95% charged is estimated to be 2.4 pH units (FIG. 3). Conversely, the magnitude of the $pK_a$ shift required to induce a similar change in charge density is approximately 2.6 units.

Figure 4:
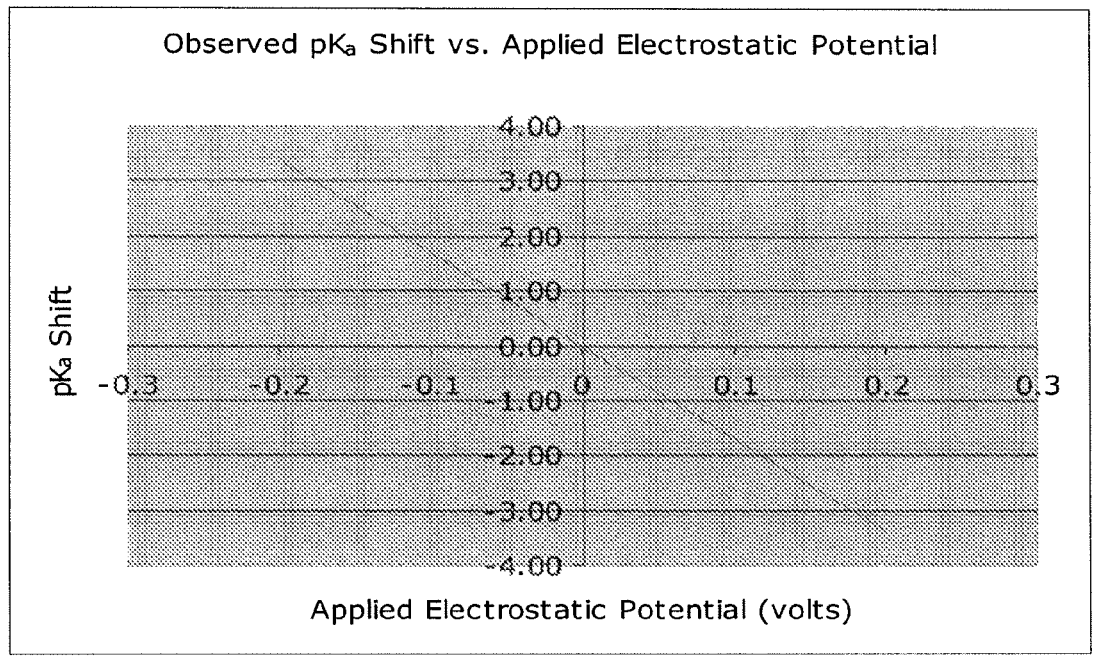
FIG. 4 graphs the observed shift in pKa as a function of the strength of an applied electric field.

FIG. 4 graphs an estimate of the magnitude of the expected $pK_a$ shift for a given applied electrostatic potential. The estimate was created using the equation given by Forsyth, et al (2002), Proteins: Struct. Funct. Genet. 48:388-403:

$$pK_{observed} = pK_{model} - V/2.3RT$$

where $PK_{observed}$=the observed pKa
$pK_{model}$=the pKa for model compounds
V=the electrostatic potential (kcal/mol e-)
R=the gas constant ($1.987 \times 10^{-3}$ kcal/mol/degree K)
T=absolute temperature This use of this equation is an oversimplification as it ignores contributions from the electrical double layer, desolvation effects, polarization effects, and the reaction field resulting from introduction of charge near a dielectric boundary, however it has been shown to provide a qualitatively correct description of the $pK_a$ shifts observed for carboxyl groups in proteins (plots of experimental pKa values versus applied potential exhibited smaller slopes than predicted by the simple equation above). As can be seen in FIG. 4, relatively small applied electrostatic potentials can be expected to induce significant $pK_a$ shifts.

Many proteins, peptides, cofactors, and other bio-molecules bear positive charges at lower pH. Devices of the present invention may be used to extract positively charged molecules from solution. By creating a negative charge on the extraction surface through the application of an electric field, positively charged molecules are encouraged to adsorb to the surface of the channel or pillar array. Reversing the applied electric field causes the molecules to de-adsorb.

In general, the types of nucleic acids that can be extracted include polymers of deoxyribonucleotides (DNA) or ribonucleotides (RNA) and analogs thereof that are linked together by a phosphodiester bond. A polynucleotide can be a segment of a genome, a gene or a portion thereof, a cDNA, or a synthetic polydeoxyribonucleic acid sequence. A polynucleotide, including an oligonucleotide (for example, a probe or a primer) can contain nucleoside or nucleotide analogs, or a backbone bond other than a phosphodiester bond. In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine, or uracil linked to ribose. However, a polynucleotide or oligonucleotide also can contain nucleotide analogs, including non-naturally occurring synthetic nucleotides or modified naturally occurring nucleotides.

The covalent bond linking the nucleotides of a polynucleotide generally is a phosphodiester bond. However, the covalent bond also can be any of a number of other types of bonds, including a thiodiester bond, a phosphorothioate bond, a peptide-like amide bond or any other bond known to those in the art as useful for linking nucleotides to produce synthetic polynucleotides. The incorporation of non-naturally occurring nucleotide analogs or bonds linking the nucleotides or analogs can be particularly useful where the polynucleotide is to be exposed to an environment that can contain nucleolytic activity, since the modified polynucleotides can be less susceptible to degradation.

Virtually any naturally occurring nucleic acid may be sequenced including, for example, chromosomal, mitochondrial or chloroplast DNA or ribosomal, transfer, heterogeneous nuclear or messenger RNA. RNA can be converted into more stable cDNA through the use of a reverse transcription enzyme (reverse transcriptase). Additionally, non-naturally occurring nucleic acids that are susceptible to enzymatic synthesis and degredation may be used in embodiments of the present invention.

The negative charge on the nucleic acid molecule facilitates electric field assisted extraction.

In general, structures of the present invention can be fabricated from any process compatible material. Possible substrates that could be used include glass; silicon; polymers, such as for example, PDMS, polystyrene, and polyethylene; silicon nitride; silicon dioxide; and metals, such as for example, gold, aluminum, platinum, copper, silver, palladium, titanium, and the like.

Devices and methods according to the present invention can be integrated into microfluidic and nanofluidic devices that perform a variety of functions. The extraction devices and methods provide ease of fabrication and integration into microfluidic and nanofluidic chips.

Nanoscale channel refers to any void space in a surface of a substrate having a diameter in at least one direction of about one to about 500 nm. When referring to the channel, the term diameter is used in its ordinary sense, i.e., the distance across and through the middle of the channel, perpendicular to the axis of the channel, and parallel to the plane of the substrate in which the channel is disposed. When referring to a channel (s), however, the term diameter is not intended to limit the cross-sectional shape of the channel(s) to a circle, as any channel shape can be employed. Microscale refers to channels having a diameter of 500 μm or less.

There are numerous suitable methods for patterning an array of nanoscale features on a surface of a substrate. Examples of such suitable methods include lithography methods such as, for example, interferometric lithography (IL), immersion interferometric lithography, electron beam lithography, scanning probe lithography, nanoimprint, extreme ultraviolet lithography, and X-ray lithography, and stamping, etching, microetching, and molding techniques. The technique used will depend in part on the composition and shape of the substrate. Generally, lithography is a highly specialized printing process used to create detailed patterns on a substrate, such as a silicon wafer. An image containing a desired pattern is projected onto the wafer, which is coated by a thin layer of photosensitive material called resist. The bright parts of the image pattern cause chemical reactions which, in turn, render the resist material soluble, and, thus, dissolve away in a developer liquid, whereas the dark portions of the image remain insoluble. After development, the resist forms a stenciled pattern across the wafer surface, which accurately matches the desired pattern. Finally, the pattern is permanently transferred into the wafer surface, for example by a chemical etchant, which etches (removes) those parts of the surface unprotected by the resist.

In various embodiments of the invention, arrays may be incorporated into a larger apparatus and/or system. In certain embodiments, the substrate may be incorporated into a microelectro-mechanical system (MEMS). MEMS are integrated systems comprising mechanical elements, sensors, actuators, and electronics. All of those components may be manufactured by known microfabrication techniques on a common chip, comprising a silicon-based or equivalent substrate (See for example, Voldman et al., *Ann. Rev. Biomed. Eng.*, 1:401-425 (1999).) The sensor components of MEMS may be used to measure mechanical, thermal, biological, chemical, optical and/or magnetic phenomena. The electronics may process the information from the sensors and control actuator components such as pumps, valves, heaters, coolers, and filters, thereby controlling the function of the MEMS.

In some embodiments of the invention, substrates may be connected to various fluid filled compartments, such as microfluidic channels, nanochannels, and or microchannels. These and other components of the apparatus may be formed as a single unit, for example in the form of a chip, such as semiconductor chips and or microcapillary or microfluidic chips. Alternatively, the substrates may be removed from a silicon wafer and attached to other components of an apparatus. Any materials known for use in such chips may be used in the disclosed apparatus, including silicon, silicon dioxide, silicon nitride, polydimethyl siloxane (PDMS), polymethylmethacrylate (PMMA), plastic, glass, and quartz.

Techniques for batch fabrication of chips are well known in the fields of computer chip manufacture and or microcapillary chip manufacture. Such chips may be manufactured by any method known in the art, such as by photolithography and etching, laser ablation, injection molding, casting, molecular beam epitaxy, dip-pen nanolithography, chemical vapor deposition (CVD) fabrication, electron beam or focused ion beam technology or imprinting techniques. Non-limiting examples include conventional molding with a flowable, optically clear material such as plastic or glass; photolithography and dry etching of silicon dioxide; electron beam lithography using polymethylmethacrylate resist to pattern an aluminum mask on a silicon dioxide substrate, followed by reactive ion etching. Methods for manufacture of nanoelectromechanical systems may be used for certain embodiments of the invention. See for example, Craighead, *Science,* 290:1532-36, (2000). Various forms of microfabricated chips are commercially available from, for example, Caliper Technologies Inc. (Mountain View, Calif.) and ACLARA BioSciences Inc. (Mountain View, Calif.).

We claim:

1. A device comprising:
   a first substrate having an array of pillars on a surface wherein the array of pillars is coated with an insulating coating and the pillars comprise an electrode within the insulating coating;
   a second substrate having an array of pillars on a surface wherein the array of pillars is coated with an insulating coating and the pillars comprise an electrode within the insulating coating;
   wherein the surface of the first substrate having an array of pillars is in proximity to the surface of the second substrate such that the array of pillars of the first substrate and the array of pillars of the second substrate interdigitate and create a channel between the pillars of the first and second substrate; and
   wherein the channel between the pillars of the first and second substrate has a dimension that is less than 50 μm.

2. The device of claim 1 wherein the insulating coating is a polymer.

3. The device of claim 1 wherein the insulating coating is selected from the group consisting of $SiO_2$, $ZrO_2$, $HfO_2$, hafnium silicates, zirconium silicates, $Al_2O_3$, $La_2O_3$, and $Y_2O_3$.

4. The device of claim 1 wherein the substrate is comprised of silicon.

5. The device of claim 1 wherein the first or the second substrate comprises a second channel that allows a liquid to flow into and out of a first channel between the pillars of the first and second substrates.

6. The device of claim 1 wherein the device is capable of creating an electric field between the pillars of the first substrate and the pillars of the second substrate through the application of an electric potential difference across electrodes within the insulating coating of the pillars of the first substrate and electrodes within the insulating coating of the pillars of the second substrate.

7. The device of claim 1 wherein the electrodes are comprised of metal.

\* \* \* \* \*